United States Patent [19]

Yanaihara et al.

[11] Patent Number: 4,530,836
[45] Date of Patent: Jul. 23, 1985

[54] PEPTIDE

[75] Inventors: Noboru Yanaihara, Shizuoka; Nobuo Sugiura, Hajima; Kazuhisa Kashimoto, Kasugai, all of Japan

[73] Assignee: Amano Pharmaceutical Co., Ltd., Nagoya, Japan

[21] Appl. No.: 611,538

[22] Filed: May 17, 1984

[30] Foreign Application Priority Data

May 31, 1983 [JP] Japan .................................. 58/97718
Nov. 4, 1983 [JP] Japan .................................. 58/208066

[51] Int. Cl.³ ..................... A61K 37/00; C07C 103/52
[52] U.S. Cl. ................................ 514/16; 260/112.5 R
[58] Field of Search .................. 260/112.5 R; 424/177

[56] References Cited

U.S. PATENT DOCUMENTS 3,892,726  7/1975  Ondetti et al. ............... 260/112.5 R
4,351,829  9/1982  Zetler et al. ......................... 424/177
4,400,377  8/1983  Zetler et al. ......................... 424/177

OTHER PUBLICATIONS

Zetler, Peptides, vol. 3, pp. 701–704, 1982.
Chem. Abstr. vol. 76, (1972) 81436r.

Primary Examiner—Delbert R. Phillips
Attorney, Agent, or Firm—Wegner & Bretschneider

[57] ABSTRACT

Novel peptides represented by the following formula $$R_1-A-B-C-D-Trp-Met-Y \qquad (1)$$

wherein; $R_1$ denotes pGlu, $X-R_2-CO-$, X being carboxyl or amino and $R_2$ being lower alkylene of 1–6 carbon atoms, or

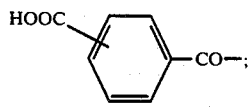

A denotes Asp, Ala, or merely a chemical bond; B denotes $Tyr(SO_3H)$ or $Phe(NHSO_3H)$; C denotes Met or merely a chemical bond; D denotes Gly, D—Ala, or D—Trp; and Y denotes $NH_2$, Asp—$NH_2$, or Asp—Phe—$NH_2$; with the proviso that Y is $NH_2$ or Asp—$NH_2$ when $R_1$ is pGlu, $HOOC-R_2-CO-$, or

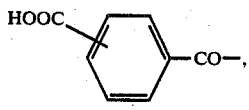

B is $Tyr(SO_3H)$, C is Met, and D is Gly, and pharmacologically acceptable salts thereof.

19 Claims, 4 Drawing Figures

PEPTIDE

BACKGROUND OF THE INVENTION

1. Field of the Invention

This invention relates to novel peptides.

2. Description of the Prior Art

As regards peptides analogous to the peptide of the invention, there is known for example a peptide represented by formula

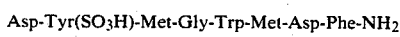
Asp-Tyr(SO$_3$H)-Met-Gly-Trp-Met-Asp-Phe-NH$_2$ (hereinafter this peptide is referred to as "CCK-8"). CCK-8 is known to have a wide variety of physiological actions such as the contraction of gallbladder, stimulation of pancreatic enzyme secretion, stimulation of pancreatic internal secretion, potentiation of intestinal movement, depression of gastric secretion, pancreas proliferation, depression of central nervous system, sedation, enhancement of sleeping time, antipsychopathia action, anti convoulsive action, analgesia, and anorexia.

SUMMARY OF THE INVENTION

It is an object of the present invention to provide novel peptides of the follwoing formula (1) and pharmacologically acceptable salts thereof, which can be obtained in a high yield and high purity, R$_1$-A-B-C-D-Trp-Met-Y     (1)

wherein; R$_1$ denotes pGlu, X—R$_2$—CO—, X being carboxyl or amino and R$_2$ being lower alkylene of 1–6 carbon atoms, or

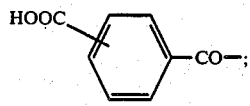

A denotes Asp, Ala, or merely a chemical bond; B denotes Tyr(SO$_3$H) or Phe(NHSO$_3$H); C denotes Met or merely a chemical bond; D denotes Gly, D-Ala, or D-Trp; and Y denotes NH$_2$, Asp-NH$_2$, or Asp-Phe-NH$_2$; with the proviso that Y is NH$_2$ or Asp-NH$_2$ when R$_1$ is pGlu, HOOC—R$_2$—CO—, or

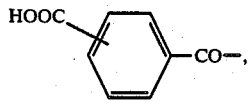

B is Tyr(SO$_3$H), C is Met, and D is Gly.

It is another object of the present invention to provide a pharmaceutical composition useful for accelerating the pancreatic function, which comprises an effective amount of formula (1) or pharmacologically acceptable salts thereof.

According to one aspect of the present invention, there is provided novel peptides represented by the following formula R$_1$-A-B-C-D-Trp-Met-Y     (1)

wherein; R$_1$ denotes pGlu, X—R$_2$—CO—, X being carboxyl or amino and R$_2$ being lower alkylene of 1–6 carbon atoms, or

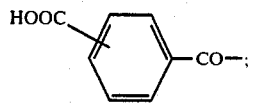

A denotes Asp, Ala, or merely a chemical bond; B denotes Tyr(SO$_3$H) or Phe(NHSO$_3$H); C denotes Met or merely a chemical bond; D denotes Gly, D-Ala, or D-Trp; and Y denotes NH$_2$, Asp-NH$_2$, or Asp-Phe-NH$_2$; with the proviso that Y is NH$_2$ or Asp-NH$_2$ when R$_1$ is pGlu, HOOC—R$_2$—CO—, or

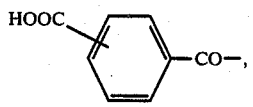

B is Tyr(SO$_3$H), C is Met, and D is Gly, and pharmacologically acceptable salts thereof.

According to another aspect of the present invention, there is provided a process for the preparation of novel peptides represented by the following formula R$_1$-A-Tyr(SO$_3$H)-C-D-Trp-Met-Y     (6)

wherein; R$_1$ denotes pGlu, X—R$_2$—CO—, X being carboxyl or amino and R$_2$ being lower alkylene of 1–6 carbon atoms, or

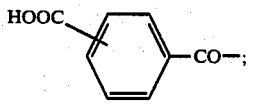

A denotes Asp, Ala, or merely a chemical bond; C denotes Met or merely a chemical bond; D denotes Gly, D-Ala, or D-Trp; and Y denotes NH$_2$, Asp-NH$_2$, or Asp-Phe-NH$_2$; with the proviso that Y is NH$_2$ or Asp-NH$_2$ when R$_1$ is pGlu, HOOC—R$_2$—CO—, or

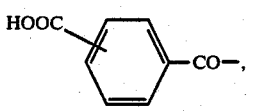

C is Met, and D is Gly, and pharmacologically acceptable salts thereof, characterized in that the Tyr-residue in the peptide of the following formula R$_1$-A-Tyr-C-D-Trp-Met-Y     (2)

wherein; R$_1$, A, C, D, and Y are the same as defined above, or the peptide in which active groups such as amino groups are protected by suitable protecting groups is subjected to the sulfate-ester reaction to convert the Tyr-residue to Tyr(SO$_3$H) residue.

According to further an aspect of the present invention, there is provided a process for the preparation of novel peptides represented by the following formula R$_1$-A-Tyr(SO$_3$H)-C-D-Trp-Met-Y     (6)

wherein; $R_1$ denotes pGlu, $X-R_2-CO-$, X being carboxyl or amino and $R_2$ being lower alkylene of 1-6 carbon atoms, or

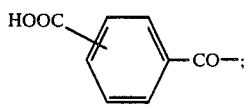

A denotes Asp, Ala, or merely a chemical bond; C denotes Met or merely a chemical bond; D denotes Gly, D-Ala, or D-Trp; and Y denotes $NH_2$, Asp-$NH_2$, or Asp-Phe-$NH_2$; with the proviso that Y is $NH_2$ or Asp-$NH_2$ when $R_1$ is pGlu, $HOOC-R_2-CO-$, or

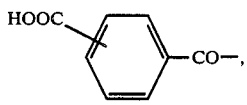

C is Met, and D is Gly, and pharmacologically acceptable salts thereof, characterized in that a sulfo group of a protected peptide amide sulfate ester obtained by the sulfate-ester reaction of the Tyr residue in the protected peptide of the following formula

$R_1$-A-Tyr-C-D-Trp-Met-Y (2)

wherein $R_1$, A, C, D, and Y are the same as defined above, is converted to a salt of divalent metals such as Ca, Zn, and the like to stabilize said protected peptide amide sulfate ester, and thereafter said protected peptide amide sulfate ester is deprotected.

According to still further an aspect of the present invention, there is provided a process for the preparation of novel peptides represented by the following formula

$R_1$-A-Phe(NHSO$_3$H)-C-D-Trp-Met-Y (6)

wherein; $R_1$ denotes pGlu, $X-R_2-CO-$, X being carboxyl or amino and $R_2$ being lower alkylene of 1-6 carbon atoms, or

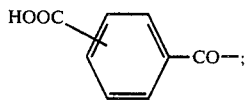

A denotes Asp, Ala, or merely a chemical bond; C denotes Met or merely a chemical bond; D denotes Gly, D-Ala, or D-Trp, and pharmacologically acceptable salts thereof, characterized in that a divalent metal salt of a sulfonated p-amino phenylalanine derivative is prepared, and a peptide chain is elongated by use of said divalent metal salt.

According to still further an aspect of the present invention, there is provided an accelerator for pancreatic function which contains a novel peptide represented by the following formula

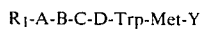

$R_1$-A-B-C-D-Trp-Met-Y (1)

wherein; $R_1$ denotes pGlu, $X-R_2-CO-$, X being carboxyl or amino and $R_2$ being lower alkylene of 1-6 carbon atoms, or

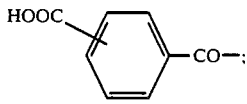

A denotes Asp, Ala, or merely a chemical bond; B denotes Tyr(SO$_3$H) or Phe(NHSO$_3$H); C denotes Met or merely a chemical bond; D denotes Gly, D-Ala, or D-Trp; and Y denotes $NH_2$, Asp-$NH_2$, or Asp-Phe-$NH_2$; with the proviso that Y is $NH_2$ or Asp-$NH_2$ when $R_1$ is pGlu, $HOOC-R_2-CO-$, or

B is Tyr(SO$_3$H), C is Met, and D is Gly, and pharmacologically acceptable salts thereof, as an effective component.

According to still further an aspect of the present invention, there is provided a reagent for pancreatic function tests or a contrast medium for gallbladder which contains a novel peptide represented by the following formula

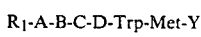

$R_1$-A-B-C-D-Trp-Met-Y (1)

wherein; $R_1$ denotes pGlu, $X-R_2-CO-$, X being carboxyl or amino and $R_2$ being lower alkylene of 1-6 carbon atoms, or

A denotes Asp, Ala, or merely a chemical bond; B denotes Tyr(SO$_3$H) or Phe(NHSO$_3$H); C denotes Met or merely a chemical bond; D denotes Gly, D-Ala, or D-Trp; and Y denotes $NH_2$, Asp-$NH_2$, or Asp-Phe-$NH_2$; with the proviso that Y is $NH_2$ or Asp-$NH_2$ when $R_1$ is pGlu, $HOOC-R_2-CO-$, or

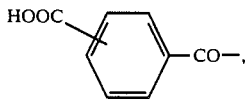

B is Tyr(SO$_3$H), C is Met, and D is Gly, and pharmacologically acceptable salts thereof as an effective component.

DETAILED DESCRIPTION OF THE PREFERRED EMBODIMENTS

Figure 1:
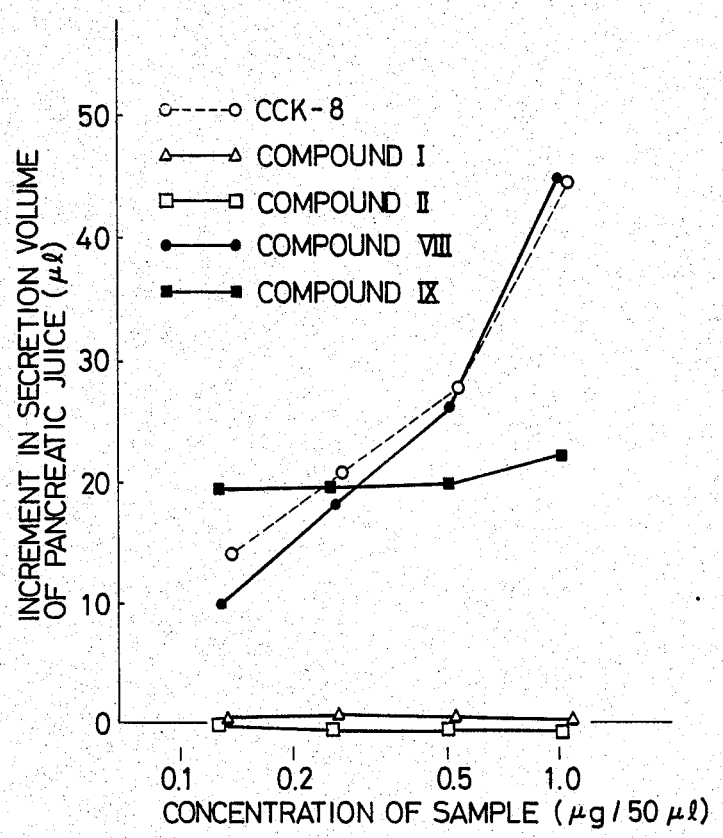
FIGS. 1 and 2 show pancreatic secretion accelerating activities of various peptides of the present invention compared with that of CCK-8.

The peptide of the present invention is novel and represented by the general formula R$_1$-A-B-C-D-Trp-Met-Y     (1)

wherein; R$_1$ denotes pGlu, X—R$_2$—CO—, X being carboxyl or amino and R$_2$ being lower alkylene, or

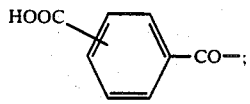

A denotes Asp, Ala, or merely a chemical bond (this means that R$_1$ combines directly with B); B denotes Tyr (SO$_3$H) or Phe(NHSO$_3$H); C denotes Met or merely a chemical bond (this means that B combines directly with D); D denotes Gly, D-Ala, or D-Trp; and Y denotes NH$_2$, Asp-NH$_2$, or Asp-Phe-NH$_2$; with the proviso that Y is NH$_2$ or Asp—NH$_2$ when R$_1$ is pGlu, HOOC—R$_2$—CO— or

B is Tyr(SO$_3$H), C is Met, and D is Gly.

In the present specification, the abbreviations of amino acids, peptides, protective groups, active groups, and other compounds and groups are in accordance with those defined in IUPAC or IUB or with those customarily used in the art. Examples of the abbreviations are given below. Unless otherwise specified, compounds such as amino acids, when they can involve optical isomers, refer to L-isomers thereof.

| | |
|---|---|
| Asp | Aspartic acid residue |
| Ala | Alanine residue |
| β-Ala | β-Alanine residue |
| Leu | Leucine residue |
| Gly | Glycine residue |
| Met | Methionine residue |
| pGlu | Pyroglutamic acid residue |
| Phe | Phenylalanine residue |
| Trp | Tryptophan residue |
| Tyr | Tyrosine residue |
| Bz | Benzyl group |
| Boc | tert-Butyloxycarbonyl group |
| Z | Benzyloxycarbonyl group |
| OSu | Succinimidoxy group |
| Suc | HOOC—(CH$_2$)$_2$—CO— |
| Glt | HOOC—(CH$_2$)$_3$—CO— |
| Pht | (phthaloyl structure with COOH and CO—) |
| DMF | Dimethylformamide |
| THF | Tetrahydrofuran |

The peptide of the general formula (1) can be prepared by common methods applied for the synthesis of peptides, for example, methods described in "The Peptides", Vol. 1 (1966) (by Schroder and Luhke, published by Academic Press, New York, U.S.A) and "Peptide Synthesis" (1975) (by Izumiya et al., published by Maruzen Co., Ltd.). These processes, applicable in the invention, include the azide method, acid chloride method, acid anhydride method, mixed anhydride method, DCC method, active ester method (p-nitrophenyl ester method, N-hydroxysuccimide ester method, cyanomethyl ester method, or the like, the method employing Woodward's reagent K, carbodiimidazole method, oxidation-reduction method, DCC-additive method (HONB, HOBT, HOSu), and solid phase method, etc.

Usually, the peptide of the general formula (1) is prepared according to the above-mentioned general method for the synthesis of polypeptides, for instance, the so-called stepwise process which comprises successive condensations of individual amino acids with a terminal amino acid or the process which comprises coupling reactions of a few fragments to complete the intended polypeptide. More particularly, the present peptide can be prepared by the condensation of a reactive-carboxyl-containing compound with a reactive-amino-containing compound in the usual way, the former compound corresponding to one of the two moieties into which the peptide can be divided by cutting its main chain at an arbitrary position and the latter compound corresponding to the other moiety. When the condensation product has protective groups, the preparation is possible through eliminating the protective groups in the usual way. Aspartic acid, when used in the reaction process for synthesizing the peptide of the formula (1) is desired in most cases to be protected previously. In the final step of the reaction process, all the protective groups are usually eliminated from the peptide in which one or more of the constituent amino acid residues are protected.

In the reaction process for synthesizing the peptide of the formula (1), the functional groups which should not participate in the reaction are also protected by common protective groups, which are eliminated after completion of the reaction. Moreover, the functional groups to participate in the reaction are activated in general.

The above reaction methods are known and reagents used therein can be suitably selected from known compounds.

Protective groups for the amino group include, for example, carbobenzoxy (hereinafter abbreviated as Z), tert-butyloxycarbonyl (hereinafter abbreviated as Boc), tert-amyloxycarbonyl, isobornyloxycarbonyl, p-methoxybenzyloxycarbonyl, 2-chloro-benzyloxycarbonyl, adamantyloxycarbonyl, trifluoroacetyl, phthalyl, formyl, o-nitrophenylsulphenyl, and diphenylphosphinothioyl, etc. Protective groups for the carboxyl group include, for example, alkyl esters (e.g. esters of methyl, ethyl, propyl, butyl, and tert-butyl), benzyl ester, p-nitrobenzyl ester, p-chlorobenzyl ester, benzhydryl ester, carbobenzoxyhydrazide, tert-butyloxycarbonylhydrazide, and tritylhydrazide, etc.

Activated derivatives of the carboxyl group include, for example, acid chloride, acid anhydride or mixed anhydride, azides, and activated esters (esters of pentachlorophenol, p-nitrophenol, N-hydroxysuccinimide, N-hydroxybenzotriazole, and N-hydroxy-5-norbornene-2,3-dicarboxyimide, and the like). Sometimes the peptide-linkage forming reaction can be carried out in the presence of a condensing agent such as a carbodiimide reagent (e.g., dicyclohexylcarbodiimide or carbodiimidazole) or tetraethyl pyrophosphate, etc.

In the above general formula (1), when R$_1$ is X—R$_2$—CO—(X denotes carboxyl or amino and R$_2$ denotes lower alkylene), R$_2$ denotes a C$_1$-C$_6$ alkylene. In consequence, R$_1$ in this case denotes succinyl, glutaryl, maleyl, phthalyl, glycyl, β-alanyl, γ-aminobutyryl, pyroglutaminyl, or the like. When $R_1$ is

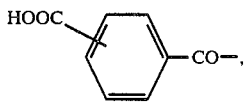

the carboxyl group can be attached to the benzene ring at any of the o-, m-, and p-positions.

The peptide of the formula (1) wherein B is Tyr($SO_3H$), i.e.,

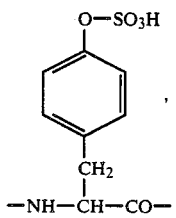

is favorably prepared in the following way:

A peptide of the general formula $R_1$-A-Tyr-C-D-Trp-Met-Y          (2)

[$R_1$, A, C, D, and Y are the same as defined in the formula (1)] which is protected if necessary by masking its active group such as amino group with a suitable protective group is synthesized, and sulfate-esterified to convert the Tyr residue into Tyr($SO_3H$).

For the peptide preparation specially requiring the elimination of a protective group after sulfate-esterification, the process disclosed in U.S. Pat. No. 4,330,466 is best suited in respect to the stabilization of the sulfate ester and the prevention of side reaction. This process comprises concentrating the sulfate-esterification reaction mixture and adding a solvent such as methanol, butanol, ethanol, dimethylformamide, or water and an aqueous solution of water-soluble salt of a divalent metal such as calcium or zinc to the concentrate to stabilize it, followed by eliminating the protective group.

The way of the sulfate-esterification is already known. For instance, the esterification is carried out by dissolving a peptide of the formula (2) in an inert solvent such as dimethylformamide or pyridine and adding a pyridine-anhydrous sulfuric acid complex in an amount of about 10 times the amount of the peptide. The reaction is preferably conducted first at a low temperature and then at room temperature, for 15–20 hours.

A peptide of the formula (1) wherein B is Phe(N-$HSO_3H$), i.e.

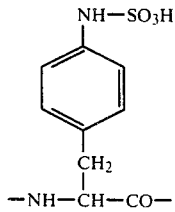

is favorably prepared in the following way:

A p-aminophenylalanine derivative of which the α-amino group is protected, e.g. Boc-Phe($NH_2$)-OH, is reacted with a sulfonating reagent, e.g. a pyridine-sulfuric anhydride complex to sulfonate the p-amino group, the Boc-Phe($NHSO_3$)-OH is converted into a divalent metal salt by reacting with a salt of divalent metal such as calcium in the same manner as mentioned above, the salt of Boc-Phe($NHSO_3^-$)-OH is condensed with a peptide fragment of the general formula C-D-Trp-Met-Y          (3)

[C, D, and Y are the same as defined in the formula (1)] by a suitable method, e.g. the active ester process, DCC process, or the like, the resulting metal salt of the peptide of the general formula Boc-Phe($NHSO_3^-$)-C-D-Trp-Met-Y          (4)

[C, D, and Y are the same as defined in the formula (1)] is treated with trifluoroacetic acid or with some other reagent to eliminate the protective group, and the resulting peptide is further condensed with the necessary acyl group and amino acid (corresponding to $R_1$ and A).

A peptide of the formula (1) wherein B is Phe(N-$HSO_3H$) is also prepared in the following way:

A peptide represented by the general formula

[$R_1$-A-Phe($NH_2$)-C-D-Trp-Met-Y]          (5)

$R_1$, A, C, D, and Y are the same as defined in the formula (1)] which is protected if necessary by masking its active group with a suitable protective group is synthesized and sulfonated to convert the Phe($NH_2$) residue into Phe($NHSO_3H$).

The thus obtained peptide of the invention, represented by the formula (1), can be desalted and purified according to common methods, for example, ion-exchange chromatography employing DEAE-Cellulose or the like, partition chromatography employing Sephadex LH-20 or Sephadex G-25, normal phase chromatography employing silica gel or the like, reversed phase chromatography employing ODS-silica gel or the like, and high performance liquid chromatography (HPLC).

Typical examples of the peptide represented by the formula (1) are as follows:

Suc-Tyr($SO_3H$)-Met-Gly-Trp-Met-$NH_2$
Suc-Asp-Tyr($SO_3H$)-Met-Gly-Trp-Met-$NH_2$
Suc-Tyr($SO_3H$)-Met-Gly-Trp-Met-Asp-$NH_2$
Suc-Tyr($SO_3H$)-Met-D-Ala-Trp-Met-Asp-Phe-$NH_2$
Suc-Tyr($SO_3H$)-Met-D-Trp-Trp-Met-Asp-Phe-$NH_2$
Suc-Phe($NHSO_3H$)-Met-Gly-Trp-Met-Asp-Phe-$NH_2$
Gly-Tyr($SO_3H$)-Met-Gly-Trp-Met-Asp-Phe-$NH_2$
β-Ala-Tyr($SO_3H$)-Met-Gly-Trp-Met-Asp-Phe-$NH_2$
pGlu-Tyr($SO_3H$)-Met-D-Trp-Trp-Met-Asp-Phe-$NH_2$
Glt-Tyr($SO_3H$)-Met-D-Trp-Trp-Met-Asp-Phe-$NH_2$
Pht-Tyr($SO_3H$)-Met-D-Trp-Trp-Met-Asp-Phe-$NH_2$
Glt-Tyr($SO_3H$)-Met-D-Ala-Trp-Met-Asp-Phe-$NH_2$
Glt-Phe($NHSO_3H$)-Met-Gly-Trp-Met-Asp-Phe-$NH_2$
Glt-Tyr($SO_3H$)-Met-Gly-Trp-Met-$NH_2$
Glt-Tyr($SO_3H$)-Met-Gly-Trp-Met-Asp-$NH_2$
Gly-Asp-Tyr($SO_3H$)-Met-Gly-Trp-Met-Asp-Phe-$NH_2$
β-Ala-Asp-Tyr($SO_3H$)-Met-Gly-Trp-Met-Asp-Phe-$NH_2$
Glt-Ala-Tyr($SO_3H$)-Gly-Trp-Met-Asp-Phe-$NH_2$
pGlu-Ala-Tyr($SO_3H$)-Gly-Trp-Met-Asp-Phe-$NH_2$

The peptide of the formula (1) can be made up into pharmaceutically acceptable salts, e.g. salts of alkali metals such as sodium and potassium, salts of alkalline earth metals such as calcium, and salts of triethylamine and ammonium.

The peptide of the invention has physiological actions similar to that of "CCK-8" of the following Asp-Tyr(SO$_3$H)-Met-Gly-Trp-Met-Asp-Phe-NH$_2$ It has been found that peptides of the present invention have properties which are not found in CCK-8, in respect to the contraction of guinea pig gallbladder, enhancement of rat pancreatic juice secretion, and stimulation of pancreatic protein secretion, among the previously mentioned physiological actions of CCK-8.

A series of peptides of the invention having D-Ala or D-Trp as D of the formula (1) exhibits almost no action on the gallbladder while having markedly strong action on the pancreas. Moreover, a series of peptides of the invention having X—R$_2$—CO— as R$_1$ wherein X is amino is lower in the activity on the pancreas though equal or higher in the activity on the gallbladder, than CCK-8. Certain peptides of the invention are 2–6 times and 50–260 times as effective as tetragastrin in the acceleration of gastric secretion and the pancreatic external secretion, respectively.

Accordingly, certain peptides of the formula (1) according to the present invention are useful as medicines for a specific organ, (for example, the accelerator for the pancreatic function) and as specific reagents for laboratory tests (for example, the pancreatic function testing reagent and a contrast medium for gallbladder) and expected also to be gastrin-like peptides. Furthermore, other peptides of the invention can be expected antagonists of CCK-8 or gastrin.

The process for producing peptides of the invention is illustrated referring to the following examples; however, the invention is not limited to these examples. Abbreviations in the examples are as defined already.

EXAMPLE 1

Preparation of Suc-Tyr(SO$_3$H)-Met-Gly-Trp-Met-NH$_2$
(Compound I)

(1) Synthesis of Boc-Trp-Met-NH$_2$ 5.78 g (0.039 mole) of H-Met-NH$_2$ was dissolved in 50 ml of DMF, then 5.46 ml of triethylamine and further 18.70 g (0.047 mole) of Boc-Trp-OSu were added under cooling with ice, and the mixture was stirred overnight at room temperature. The reaction mixture was concentrated in vacuo, and extracted with ethyl acetate. The extract was washed with 1N citric acid, saturated saline solution, saturated sodium bicarbonate solution, and saturated saline solution in series. The resulting organic layer was dried over anhydrous sodium sulfate, distilled in vacuo to remove the solvent, and solidified with hexane. The solid was recrystallized from ethyl acetate-hexane, giving 12.45 g of Boc-Trp-Met-NH$_2$; yield 73.5%, m.p. 155°–157° C.

$[\alpha]_D^{24} = -3.6°$ (C=1, methanol)

Anal. Calcd. (%) for C$_{21}$H$_{30}$N$_4$O$_4$S: C, 50.04; H, 6.96; N, 12.86. Found (%): C, 50.14; H, 7.18; N, 12.68.

(2) Synthesis of Boc-Met-Gly-Trp-Met-NH$_2$ 11.73 g (0.027 mole) of the dipeptide obtained in the above (1) was dissolved by adding 20 ml of trifluoroacetic acid containing 0.4 ml of ethanedithiol and reacted at room temperature for 30 minutes. Then, a precipitate was formed by adding 200 ml of anhydrous ether to the reaction mixture and was filtered and dried. On the other hand, 12.98 g of Boc-Met-Gly-NHNH$_2$ was dissolved in 100 ml of DMF, and after cooling with dry ice-ethanol to −20° C. or lower, was converted into azide by adding 20.25 ml of a 6N HCl-dioxane mixture and 5.44 ml of isoamyl nitrite. The reaction mixture was neutralized by further adding 17.01 ml of triethylamine, and admixed with a solution of the above deprotected dipeptide in 100 ml of DMF. The mixture was stirred at −20° C. for 2 hours and at 4° C. for 17 hours. The resulting reaction mixture was extracted with ethyl acetate similarly to the above (1), the solvent was distilled off from the extract, and the residue was solidified with ether. The solid was filtered off, dried, and recrystallized from methanol-ether, giving 12.60 g of Boc-Met-Gly-Trp-Met-NH$_2$; yield 74.9%, m.p. 200°–202° C.

$[\alpha]_D^{24} = -24.3°$ (C=1, DMF)

Anal. Calcd. (%) for C$_{28}$H$_{42}$N$_6$O$_6$S$_2$: C, 54.00; H, 6.80; N, 13.49. Found (%): C, 54.21; H, 6.81; N, 13.31.

(3) Synthesis of Boc-Tyr-Met-Gly-Trp-Met-NH$_2$

The protective group was eliminated from 6.85 g (0.011 mole) of the tetrapeptide obtained in the above (2), by using trifluoroacetic acid in the same manner as in above (2). The resulting tetrapeptide was dissolved in 50 ml of DMF, and 1.54 ml of triethylamine and 8.32 g (0.022 mole) of Boc-Tyr-OSu were added under cooling with ice. After stirring overnight at room temperature, the reaction mixture was concentrated in vacuo and extracted with ethyl acetate. The extract was concentrated, and ether was added to deposit a solid, which was then filtered, dried, and recrystallized from methanol-ethyl acetate, giving 5.46 g of Boc-Tyr-Met-Gly-Trp-Met-NH$_2$; yield 63.1%, m.p. 195°–198° C.

$[\alpha]_D^{24} = -21.8°$ (C=1, DMF)

Anal. Calcd. (%) for C$_{39}$H$_{51}$N$_7$O$_8$S$_2$: C, 56.54; H, 6.54; N, 12.47. Found (%): C, 56.67; H, 6.63; N, 12.25.

(4) Synthesis of Suc-Tyr-Met-Gly-Trp-Met-NH$_2$

The protective group was eliminated from 3.45 g (0.0044 mole) of the pentapeptide obtained in the above (3), by the same treatment as applied in the above (2). The treated pentapeptide was dissolved in DMF, and 1.23 ml of triethylamine and 0.88 g of succinic anhydride were added under cooling with ice. The mixture was stirred at room temperature for 1 day. The solvent was distilled off, 1N citric acid was added to the residue, and the resulting precipitate was filtered off, washed with water, and recrystallized from methanol-ethyl acetate, giving 2.52 g of Suc-Tyr-Met-Gly-Trp-Met-NH$_2$; yield 72.8%, m.p. 125°–127° C.

$[\alpha]_D^{24} = -28.5°$ (C=1, DMF)

Anal. Calcd. (%) for C$_{36}$H$_{47}$N$_7$O$_9$S$_2$: C, 55.02; H, 6.03; N, 12.48. Found (%): C, 54.91; H, 6.20; N, 12.42.

(5) Synthesis of Suc-Tyr(SO H)-Met-Gly-Trp-Met-NH$_2$ 1.57 g (0.002 mole) of the acylated peptide obtained in the above (4) was dissolved in a mixture of 20 ml of DMF and 2 ml of pyridine, and 3.18 g (0.020 mole) of a pyridine-sulfuric anhydride complex was added under cooling with ice. The mixture was stirred at 0° C. for 30 minutes and at room temperature for 20 hours. The reaction mixture was concentrated in vacuo, 50 ml of 0.05 M aqueous ammonium carbonate solution was added, and the pH was adjusted to 8.5 by addition of aqueous ammonia. The solution was purified by chromatography on a DEAE-Cellulose column (5×15 cm), wherein the adsorption and washing were carried out by using 1.5 l of an 0.05 M buffer solution of ammonium carbonate-amxonium bicarbonate (pH 8.5) and eluted with 2.0 l of the same but 0.2 M buffer solution (pH 8.5). Eluted fractions were measured for ultraviolet absorbance in a wavelength of 278 nm, and thereby the fractions containing the intended product were collected, concentrated, and freeze-dried, giving 0.85 g of Suc-Tyr(SO$_3$H)-Met-Gly-Trp-Met-NH$_2$ (Compound yield 50.0%).

$[\alpha]_D^{24} = -15.8°$ (C=0.5, 1N ammonia)

Anal. Calcd. (%) for $C_{36}H_{47}N_7O_{12}S_3 \cdot NH_3 \cdot H_2O$: C, 47.99; H, 5.82; N, 12.44. Found (%): C, 47.94; H, 5.59; N. 12.00.

Amino acid analysis by acidolysis: Gly 1.00 (1), Met 1.98 (2), Tyr 1.01 (1).

Infrared absorption spectroscopy of the product indicates a strong absorption peak characteristic of sulfate ester at 1050 cm$^{-1}$.

EXAMPLE 2

Preparation of Suc-Tyr(SO$_3$H)-Met-Gly-Trp-Met-Asp-NH$_2$ (Compound II)

(1) Synthesis of Boc-Met-Asp-NH$_2$ 12.47 g (0.035 mole) of Z-Asp(OBz)-NH$_2$ (m.p. 118°–120° C. $[\alpha]_D^{24} -2.6°$ (C=1, methanol). Anal. Calcd. (%) for $C_{19}H_{20}N_2O_5$: C, 64.04; H, 5.66; N, 7.86. Found (%): C, 64.04, H, 5.73, N, 7.73) was dissolved in a mixture of 300 ml of methanol and 35 ml of 1N HCl and subjected to contact reduction with hydrogen (at room temperature for 6 hours) in the presence of 1.75 g of a 10% Pd-carbon catalyst. The catalyst was then filtered off, the solvent was distilled off, and the residue was dried in vacuo. On the other hand, 9.36 g (0.035 mole) of Boc-Met-OH wa dissolved in 50 ml of THF, the solution was cooled to −20° C., and 3.85 ml of N-methylmorpholine and 4.62 ml of isobutyl chloroformate were added. The resulting mixed anhydride was admixed with a solution of the above obtained H-Asp-NH$_2$ in 50 ml of DMF (containing 4.90 ml of triethylamine). The mixture was stirred at 0° C. for 10 minutes, at 40° C. for 1 minute, and at room temperature for 20 minutes. The reaction mixture was treated in the same manner as in (1) of Example 1, giving 8.30 g of Boc-Met-Asp-NH$_2$; yield 65.2%, m.p. 226°–229° C.

$[\alpha]_D^{24} = -28.0°$ (C=1, methanol)

Anal. Calcd. (%) for $C_{14}H_{27}N_3O_7S$: C, 46.27; H, 6.93; N, 11.56. Found (%): C, 46.51; H, 7.07; N, 11.02.

(2) Synthesis of Boc-Trp-Met-Asp-NH$_2$

In the same manner as in (2) of Example 1, the protective group was eliminated from 8.00 g (0.022 mole) of the dipeptide obtained in the preceding (1), and was condensed with 10.60 g of Boc-Trp-OSu in the same manner as in (1) of Example 1. The resulting reaction mixture was concentrated in vacuo, 1N citric acid was added, and the precipitated solid was filtered and washed with water. Recrystallization thereof from methanol-ethyl acetate gave 6.45 g of Boc-Trp-Met-Asp-NH$_2$; yield 53.3%, m.p. 204°–210° C.

$[=]_D^{24} = -29.1°$ (C=1, DMF)

Anal. Calcd. (%) for $C_{25}H_{35}N_5O_7S$: C, 54.63; H, 6.42; N, 12.74. Found (%): C, 54.55; H, 6.57; N, 12.56.

(3) Synthesis of Boc-Met-Gly-Trp-Met-Asp-NH$_2$

In the same manner as in (2) of Example 1, the tripeptide obtained in the preceding (2) was condensed with 5.42 g (0.0165 mole) of Boc-Met-Gly-NHNH$_2$ according to the azide process. Then, the reaction mixture was treated in the same manner as in the preceding (2), giving 7.56 g of Boc-Met-Gly-Trp-Met-Asp-NH$_2$; yield 93.1%, m.p. 278° C.

$[\alpha]_D^{24} = -23.2°$ (C=1, DMF)

Anal. Calcd. (%) for $C_{32}H_{47}N_7O_9S_2$: C, 52.09; H, 6.42; N, 13.29. Found (%): C, 52.28; H, 6.51; N, 13.06.

(4) Synthesis of Boc-Tyr-Met-Gly-Trp-Met-Asp-NH$_2$

In the same manner as in (3) of Example 1, 2.12 g (0.0029 mole) of the pentapeptide obtained in the preceding (3) was condensed with 2.17 g (0.0057 mole) of Boc-Tyr-OSu. Then, the reaction mixture was treated in the same manner as in the preceding (2), giving 2.24 g of Boc-Tyr-Met-Gly-Trp-Met-Asp-NH$_2$; yield 86.5%, m.p. 250°–252° C.

$[\alpha]_D^{24} = -19.5°$ (C=1, DMF)

Anal. Calcd. (%) for $C_{41}H_{56}N_8O_{11}S_2 \cdot H_2O$: C, 53.43; H, 6.36; N, 12.19. Found (%): C, 53.42; H, 6.32; N, 12.15.

(5) Synthesis of Suc-Tyr-Met-Gly-Trp-Met-Asp-NH$_2$

In the same manner as in (4) of Example 1, the protective group was eliminated from 2.14 g (0.0024 mole) of the hexapeptide obtained in the preceding (4), and 0.48 g of succinic anhydride was reacted with the hexapeptide. The product was recrystallized from methanol-ethyl acetate, giving 1.65 g Suc-Tyr-Met-Gly-Trp-Met-NH$_2$; yield 77.1%, m.p. 141°–143° C.

$[\alpha]_D^{24} = -23.4°$ (C=1, DMF)

Anal. Calcd. (%) for $C_{40}H_{52}N_8O_{12}S_2 \cdot H_2O$: C, 52.27; H, 5.92; N, 12.19. Found (%): C, 52.43; H, 6.20; N, 12.23.

(6) Synthesis of Suc-Tyr(SO$_3$H)-Met-Gly-Trp-Met-Asp-NH$_2$

In the same manner as in (5) of Example 1, 1.48 g (0.00164 mole) of the acylated peptide obtained in the preceding (5) was sulfated with 2.61 g (0.0164 mole) of a pyridine-sulfuric anhydride complex. The reaction product was purified by chromatography on a DEAE-Cellulose column (5×15 cm), wherein 2.0 l of 0.3 M ammonium carbonate buffer solution (pH 8.5) was used for elution. Thus, 0.97 g of Suc-Tyr(SO$_3$H)-Met-Gly-Trp-Met-Asp-NH$_2$ (Compound II) was obtained as a lyophilized product; yield 63.6%.

$[\alpha]_D^{24} = -22.0°$ (C=1, DMF)

Anal. Calcd. (%) for $C_{40}H_{52}N_8O_{15}S_3 \cdot NH_3 \cdot 3H_2O$: C, 45.66; H, 5.84; N, 11.98. Found (%): C, 45.44; H, 5.56; N, 12.22.

Amino acid analysis by acidolysis: Asp 1.04 (1), Gly 0.98 (1), Met 1.99 (2), Tyr 0.99 (1).

Infrared absorption spectrum: 1050 cm$^{-1}$ (sulfate ester).

EXAMPLE 3

Preparation of Suc-Tyr(SO$_3$H)-Met-D-Ala-Trp-Met-Asp-Phe-NH$_2$ (Compound III)

(1) Synthesis of Boc-D-Ala-Trp-Met-Asp-Phe-NH$_2$

In the same manner as in (2) of Example 1, 24.39 g (0.035 mole) of Boc-Trp-Met-Asp-Phe-NH (m.p. 201°–203° C, $[\alpha]_D^{24} = -35.3°$ (C=1, DMF), Anal. Calcd. (%) for $C_{34}H_{44}N_6O_8S$: C, 58.61; H, 6.36; N, 12.06. Found (%): C, 58.58; H, 6.46; N, 12.02. cf. J. M. Darey et al., Journal of Chemical Society, 1966, p. 555) was treated with 70 ml of trifluoroacetic acid at room temperature for 30 minutes and precipitated by adding 500 ml of anhydrous ether. This protective-group-free peptide was dissolved in 150 ml of DMF and condensed with 7.94 g of Boc-D-Ala-OH according to the mixed anhydride process similarly to that used in (1) of Example 2. The reaction mixture was concentrated in vacuo, and 1N citric acid was added to form a precipitate, which was then washed with water and recrystallized from methanol-ether, giving 25.86 g of Boc-D-Ala-Trp-Met-Asp-Phe-NH$_2$; yield 96.2%, m.p. 219°–222° C.

$[\alpha]_D^{24} = -22.1°$ (C=1, DMF)

Anal. Calcd. (%) for C$_{37}$H$_{49}$N$_7$O$_9$S.H$_2$O: C, 56.54; H, 6.54; N, 12.48. Found (%): C, 56.42; H, 6.64; N, 12.56.

(2) Synthesis of Boc-Met-D-Ala-Trp-Met-Asp-Phe-NH$_2$

In the same manner as in the preceding (1), the protective group was eliminated from 24.57 g (0.032 mole) of the above obtained pentapeptide. The freed pentapeptide was condensed with 9.72 g of Boc-Met-OH according to the mixed anhydride process. The product was recrystallized from methanol-ether giving 19.90 g of Boc-Met-D-Ala-Trp-Met-Asp-Phe-NH$_2$; yield 69.2%, m.p. 199°–202° C.

$[\alpha]_D^{24} = -30.0°$ (C=1, DMF)

Anal. Calcd. (%) for C$_{42}$H$_{58}$N$_8$O$_{10}$S$_2$: C, 56.11; H, 6.50; N, 12.46 Found (%): C, 56.00; H, 6.93; N, 12.46.

(3) Synthesis of Boc-Tyr-Met-D-Ala-Trp-Met-Asp-Phe-NH$_2$

In the same manner as in (3) of Example 1, 9.90 g (0.011 mole) of the hexapeptide obtained in the preceding (2) was condensed with 8.23 g of Boc-Tyr-OSu. The product was recrystallized from methanol-ethyl acetate, giving 8.36 g of Boc-Tyr-Met-D-Ala-Trp-Met-Asp-Phe-NH$_2$; yield 71.5%, m.p. 202°–205° C.

$[\alpha]_D^{24} = -25.8°$ (C=1, DMF)

Anal. Calcd. (%) for C$_{51}$H$_{69}$N$_9$O$_{13}$S$_2$.H$_2$O C, 56.70; H, 6.44; N, 11.67. Found (%): C, 57.00; H, 6.54; N, 11.22.

(4) Synthesis of Suc-Tyr-Met-D-Ala-Trp-Met-Asp-Phe-NH$_2$

In the same manner as in (4) of Example 1, the protective group was eliminated from 4.02 g (0.0038 mole) of the heptapeptide obtained in the preceding (3). The deprotected heptapeptide was reacted with 0.76 g (0.0076 mole) of succinic anhydride. The product was recrystallized from methanol-ethyl acetate, giving 3.85 g of Suc-Tyr-Met-D-Ala-Trp-Met-Asp-Phe-NH$_2$; yield 95.8%, m.p. 200°–203° C.

$[\alpha]_D^{24} = -29.3°$ (C=1, DMF)

Anal. Calcd. (%) for C$_{50}$H$_{63}$N$_9$O$_{13}$S$_2$: C, 56.54; H, 5.98; N, 11.87. Found (%): C, 56.26; H, 6.36; N, 12.05.

(5) Synthesis of Suc-Tyr(SO$_3$H)-Met-D-Ala-Trp-Met-Asp-Phe-NH$_2$

In the same manner as in (6) of Example 2, 2.12 g (0.002 mole) of the Suc-Tyr-Met-D-Ala-Trp-Met-Asp-Phe-NH$_2$ obtained in the preceding (4) was sulfated and purified by chromatography on a DEAE-Cellulose column (5×15 cm). Thus, 1.25 g of Suc-Tyr(SO$_3$H)-Met-D-Ala-Trp-Met-Asp-Phe-NH$_2$ (Compound III) was obtained as a lyophilized product; yield 54.9%.

Anal. Calcd. (%) for C$_{50}$H$_{63}$N$_3$O$_{10}$S$_3$.NH$_3$.3H$_2$O: C, 49.50; H, 5.98; N, 11.54. Found (%): C, 49.67; H, 5.71; N, 11.52.

Amino acid analysis by acidolysis: Asp 1.05 (1), Gly 0.99 (1), Met 2.00 (2), Tyr 1.01 (1), Phe 1.01 (1).

Infrared absorption spectrum: 1050 cm$^{-1}$ (sulfate ester).

EXAMPLE 4

Preparation of Suc-Tyr(SO$_3$H)-Met-D-Trp-Trp-Met-Asp-Phe-NH$_2$ (Compound IV)

(1) Synthesis of Boc-D-Trp-Trp-Met-Asp-Phe-NH$_2$

In the same manner as in (1) of Example 1, 10.45 g (0.015 mole) of Boc-Trp-Met-Asp-Phe-NH$_2$ [cf. (1) of Example 3] was condensed with 9.00 g (0.022 mole) of Boc-Trp-OSu. The resulting reaction liquid was concentrated, and a precipitate was formed by adding 1N citric acid and washed with water. Recrystallization thereof from methanol-water gave 8.09 g of Boc-D-Trp-Trp-Met-Asp-Phe-NH$_2$; yield 61.1%, m.p. 225°–227° C.

$[\alpha]_D^{24} = -24.0°$ (C=1, DMF)

Anal. Calcd. (%) for C$_{45}$H$_{54}$N$_8$O$_9$S: C, 61.21; H, 6.16; N, 12.69. Found (%): C, 61.44; H, 6.30; N, 12.55.

(2) Synthesis of Boc-Met-D-Trp-Trp-Met-Asp-Phe-NH$_2$

In the same manner as in (2) of Example 3, 7.94 g (0.009 mole) of the pentapeptide obtained in the preceding (1) was condensed with 3.37 g of Boc-Met-OH. The product was recrystallized from methanol-water, giving 7.00 g of Boc-Met-D-Trp-Trp-Met-Asp-Phe-NH$_2$; yield 76.7%, m.p. 195°–197° C.

$[\alpha]_D^{24} = -28.1°$ (C=1, DMF)

Anal. Calcd. (%) for C$_{50}$H$_{63}$N$_9$O$_{10}$S$_2$: C, 59.21; H, 6.26; N, 12.43. Found (%): C, 59.08; H, 6.37; N, 12.24.

(3) Synthesis of Boc-Tyr-Met-D-Trp-Trp-Met-Asp-Phe-NH$_2$

In the same manner as in (3) of Example 1, 3.55 g (0.0035 mole) of the hexapeptide obtained in the preceding (2) was freed of the protective group and then condensed with 2.65 g of Boc-Tyr-OSu. The product was recrystallized from methanol-water, giving 3.51 g of Boc-Tyr-Met-D-Trp-Trp-Met-Asp-Phe-NH$_2$; yield 85.2%, m.p. 204°–206° C.

$[\alpha]_D^{24} = -26.3°$ (C=1, DMF)

Anal. Calcd. (%) for C$_{59}$H$_{92}$N$_{10}$O$_{12}$S$_2$: C, 60.19; H, 6.16; N, 11.90. Found (%): C, 59.93; H, 6.28; N, 11.35.

(4) Synthesis of Suc-Tyr-Met-D-Trp-Trp-Met-Asp-Phe-NH$_2$

In the same manner as in (4) of Example 1, 3.41 g (0.0029 mole) of the heptapeptide obtained in the preceding (3) was deprotected, and then reacted with 0.58 g of succinic anhydride. The product was recrystallized from methanol-ether, giving 3.17 g of Suc-Tyr-Met-D-Trp-Trp-Met-Asp-Phe-NH$_2$; yield 92.8%, m.p. 198°–201° C.

$[\alpha]_D^{24} = -31.1°$ (C=1, DMF)

Anal. Calcd. (%) for C$_{58}$H$_{68}$N$_{10}$O$_{13}$S$_2$: C, 59.17; H, 5.82; N, 11.90. Found (%): C, 59.40; H, 6.06; N, 11.75.

(5) Synthesis of Suc-Tyr(SO$_3$H)-Met-D-Trp-Trp-Met-Asp-Phe-NH$_2$

In the same manner as in (5) of Example 1, 2.36 g (0.002 mole) of the acylated peptide obtained in the preceding (4) was sulfated with 3.18 g of a pyridine-sulfuric anhydride complex. The product was purified by chromatography on a DEAE-Cellulose column (5×15 cm), wherein 2 l of a 30% methanol-0.5 M ammonium carbonate buffer solution (pH 8.5) was used for elution. Thus, 1.28 g of Suc-Tyr(SO$_3$H)-Met-D-Trp-Trp-Met-Asp-Phe-NH$_2$ (Compound IV) was obtained as a lyophylized product; yield 50.9%.

$[\alpha]_D^{24} = -15.0°$ (C=1, 1N ammonia)

Anal, Calcd. (%) for $C_{58}H_{68}N_{10}O_{16}S_3 \cdot NH_3 \cdot 3H_2O$: C, 52.44; H, 5.84; N, 11.60. Found (%): C, 52.21; H, 5.71; N, 11.91.

Amino acid analysis by acidolysis:

Asp 1.03 (1), Met 1.98 (2), Tyr 1.00 (1), Phe 0.99 (1).

EXAMPLE 5

Preparation of
Glt-Tyr(SO$_3$H)-Met-D-Trp-Trp-Met-Asp-Phe-NH$_2$
(Compound V)

Similarly to (4) of Example 4, 1.77 g (0.0015 mole) of the Boc-Tyr-Met-D-Trp-Trp-Met-Asp-Phe-NH$_2$ obtained in (3) of Example 4 was deprotected and reacted with 0.342 g of glutaric anhydride. The product was recrystallized from methanol-ether, giving 1.50 g of Glt-Tyr-Met-D-Trp-Trp-Met-Asp-Phe-NH$_2$: yield 83.9%, m.p. 208°–210° C.

$[\alpha]_D^{24} = -25.7°$ (C=1, DMF)

Anal. Calcd. (%) for $C_{59}H_{70}N_{10}O_{13}S_2 \cdot H_2O$: C, 58.60; H, 6.00; N, 11.58. Found (%): C, 58.49; H, 6.08; N, 11.52.

Similarly to (5) of Example 4, 1.30 g of the above peptide was sulfated and purified by chromatography on a DEAE-Cellulose column (4×15 cm). Thus, 683 mg of Glt-Tyr(SO$_3$H)-Met-D-Trp-Trp-Met-Asp-Phe-NH$_2$ (Compound V) was obtained as a lyophilized product; yield 49.3%.

Anal. Calcd. (%) for $C_{59}H_{70}N_{10}O_{16}S_3 \cdot NH_3 \cdot 4H_2O$: C, 52.09; H, 6.00; N, 11.32. Found (%): C, 51.92; H, 6.11; N, 11.33.

Amino acid analysis by acidolysis:

Asp 1.05 (1), Met 1.94 (2), Tyr 1.03 (1), Phe 0.98 (1).

EXAMPLE 6

Preparation of
Pht-Tyr(SO$_3$H)-Met-D-Trp-Trp-Met-Asp-Phe-NH$_2$

Similarly to (4) of Example 4, 1.77 g (0.0015 mole) of the Boc-Tyr-Met-D-Trp-Trp-Met-Asp-Phe-NH$_2$ obtained in (3) of Example 4 was deprotected and condensed with 0.444 g of phthalic anhydride. The resulting product was recrystallized from methanol-ether, giving 1.79 g of Pht-Tyr-Met-D-Trp-Trp-Met-Asp-Phe-NH$_2$; yield 97.4%, m.p. 180°–183° C.

$[\alpha]_D^{24} = -31.4°$ (C=1, DMF)

Anal. Calcd. (%) for $C_{62}H_{68}N_{10}O_{13}S_2 \cdot H_2O$: C, 59.89; H, 5.67; N, 11.26. Found (%): C, 59.55; H, 5.97; N, 11.45.

Similarly to (5) of Example 4, 1.59 g of the above peptide was sulfated and purified by chromatography on a DEAE-Cellulose column (4×15 cm). Thus, 638 mg of Pht-Tyr(SO$_3$H)-Met-D-Trp-Trp-Met-Asp-Phe-NH$_2$ (Compound VI) was obtained as a lyophilized product; yield 37.6%.

$[\alpha]_D^{24} = -18.3°$ (C=1, 1N ammonia)

Anal. Calcd. (%) for $C_{62}H_{68}N_{10}O_{16}S_3 \cdot NH_3 \cdot 4H_2O$: C, 53.40; H, 5.71; N, 11.05. Found (%): C, 53.61; H, 5.65; N, 10.59.

Amino acid analysis by acidolysis:

Asp 1.06 (1), Met 1.98 (2), Tyr 0.96 (1), Phe 0.99 (1).

EXAMPLE 7

Preparation of
Suc-Phe(NHSO$_3$H)-Met-Gly-Trp-Met-Asp-Phe-NH$_2$
(Compound VII)

(1) Synthesis of Boc-Phe(NH$_2$)-OH 3.27 g (0.014 mole) of H-Phe(NO$_2$)-OH and 3.26 ml of triethylamine were dissolved in 50 ml of water, and 50 ml of a dioxane solution of 4.10 g (0.017 mole) of a Boc-S reagent, e.g. t-butyl S-4,6-dimethyl pyrimidin-2-yl thiolcarbonate (made by Kokusan Kagaku Co., Ltd.) was added under cooling with ice. After one day stirring at room temperature, the reaction mixture was diluted with 50 ml of water and washed with ethyl acetate. The aqueous layer, cooled with ice, was acidified to pH 2 by adding 6N HCl. The mixture was extracted with ethyl acetate, and the extract was washed with 1N HCl and then saturated saline solution, and dried over anhydrous sodium sulfate. The ethyl acetate was distilled off in vacuo, hexane was added to the residue, and the solid deposit was filtered and dried. Recrystallization thereof from ethyl acetate-hexane gave 4.04 g of Boc-Phe(NO$_2$)-OH; yield 84.0%, m.p. 110°–112° C.

$[\alpha]_D^{24} = +7.7°$ (C=1, methanol)

Anal. Calcd. (%) for $C_{14}H_{18}N_2O_6$: C, 54.19; H, 5.85; N, 9.03. Found (%): C, 54.13; H, 5.77; N, 9.10.

3.93 g (0.013 mole) of the above obtained Boc-Phe(NO$_2$)-OH was dissolved in 50 ml of methanol and hydrogenated over 1.3 g of a 5% Pd-carbon catalyst at room temperature for 8 hours. Then, the catalyst was filtered off, and the filtrate was concentrated in vacuo. Hexane was added to the residual to form a precipitate, which was then recrystallized from ethyl acetate-ether, giving 2.39 g of Boc-Phe(NH$_2$)-OH; yield 67.1%, m.p. 126°–128° C.

$[\alpha]_D^{24} = +26.6°$ (C=1, methanol)

Anal. Calcd. (%) for $C_{14}H_{20}N_2O_4$: C, 59.99; H, 7.19; N, 9.99. Found (%): C, 59.79; H, 7.15; N, 9.85.

(2) Synthesis of Boc-Phe(NHSO$_3^-$)-O$^-$·calcium salt 1.26 g (0.0045 mole) of the Boc-Phe(NH$_2$)-OH obtained in the preceding (1) was dissolved in a mixture of 20 ml of DMF and 2 ml of pyridine, and 3.58 g of a pyridine-sulfuric anhydride complex was added under cooling with ice. The mixture was stirred at 0° C. for 30 minutes and then at room temperature for 20 hours. The resulting reaction mixture was concentrated in vacuo, 30 ml of ice-cold water was added to the residue to dissolve it, and 27 ml of 1 M aqueous calcium acetate solution was added immediately. The resulting calcium sulfate precipitate was removed by centrifugation, carbon dioxide gas was blown into the supernatant, and the resulting calcium carbonate precipitate was removed by centrifugation. The resulting supernatant was concentrated in vacuo. The residue was recrystallized from ethanol-ether, giving Boc-Phe(NHSO$_3^-$)-O$^-$·Ca$^{2+}$.

(3) Synthesis of Boc-Phe(NHSO$_3$H)-Met-Gly-Trp-Met-Asp-Phe-NH$_2$ 1.71 g (0.0045 mole) of the sulfonated amino acid obtained in the preceding (2) was dissolved in 20 ml of DMF, then 0.57 g of N-hydroxysuccinimide and 0.93 g of dicyclohexylcarbodiimide were added, and the mixture was stirred overnight at 4° C. The precipitated urea compound was filtered off, the filtrate was concentrated in vacuo, ether was added to the residue, and the resulting precipitate was filtered and dried, giving Boc-Phe(NHSO$_3^-$)-OSu·½Ca salt.

On the other hand, 2.66 g (0.003 mole) of Boc-Met-Gly-Trp-Met-Asp-Phe-NH$_2$ [m.p. 195°–197° C. $[\alpha]_D^{24} = -30.0°$ (C=1, DMF). Anal. Calcd. (%) for $C_{41}H_{56}N_8O_{12}S_2$: C, 55.64; H, 6.38; N, 12.66. Found (%): C, 55.85; H, 6.55; N, 12.54. cf. M. A. Ondett et al., Jounal of the Americal Chemical Society, 92, 195 (1970)] was dissolved in 6 ml of trifluoroacetic acid containing 0.2 ml of ethandithiol, and the solution was allowed to stand at room temperature for 30 minutes. Then, 70 ml of anhydrous ether was added to the reaction mixture, and the resulting precipitate was filtered and dried. The deprotected peptide was dissolved in DMF, and 0.42 ml of triethylamine was added to the solution cooled with ice.

To the resulting solution was added to the above obtained active ester [Boc-Phe(NHSO$_3$-)-OSu·½Ca salt], and the mixture was stirred overnight at room temperature. The reaction mixture was then concentrated in vacuo, and a precipitate was formed by adding ethyl acetate to the residue. The precipitate was filtered and dried, giving 2.20 g of Boc-Phe(NHSO$_3$-)-Met-Gly-Try-Met-Asp-Phe-NH$_2$·Ca salt.

(4) Synthesis of Suc-Phe(NHSO$_3$H)-Met-Gly-Trp-Met-Asp-Phe-NH$_2$

The heptapeptide calcium salt obtained in the preceding (3) was dissolved in 10 ml of trifluoroacetic acid containing 0.2 ml of ethandithiol, and the solution was allowed to stand at 0° C. for 30 minutes. To the reaction mixture was added 100 ml of anhydrous ether, and the resulting precipitate was filtered and dried. This deprotected peptide was dissolved in 30 ml of DMF, and reacted with 1.3 g of succinic anhydride in the same manner as in (4) of Example 1. The resulting reaction mixture was concentrated in vacuo, and purified in the same manner as in (5) of Example 1 by chromatography on a DEAE-Cellulose column (5×15 cm). Thus, 460 mg of Suc-Phe(NHSO$_3$H)-Met-Gly-Trp-Met-Asp-Phe-NH$_2$ (Compound VII) was obtained as a lyophilized product.

$[\alpha]_D^{25} = -17.0°$ (C=0.5, 1N ammonia)

Anal. Calcd. (%) for C$_{49}$H$_{62}$N$_{10}$O$_{15}$S$_2$·3H$_2$O: C, 49.82; H, 5.80; N, 11.86. Found (%): C, 49.63; H, 5.61; N, 11.96.

Amino acid analysis by acidolysis:

Asp 1.08 (1), Gly 1.05 (1), Met 2.04 (2), Phe 1.00 (1), Phe(NH$_2$) 0.84 (1).

EXAMPLE 8

Preparation of Gly-Asp-Tyr(SO$_3$H)-Met-Gly-Trp-Met-Asp-Phe-NH$_2$ (Compound VIII)

(1) Synthesis of Boc-Gly-Asp-Tyr-NHNH$_2$ 4.81 g (0.009 mole) of Z-Asp(OBz)-Tyr-OMe [m.p. 126°-127° C. $[\alpha]_D^{24} = -4.8°$ (C=1, methanol). Anal. Calcd. (%) for C$_{29}$H$_{30}$N$_2$O$_8$: C, 65.16; H, 5.66; N, 5.24. Found (%): C, 65.14; H, 5.71; N, 5.18] was dissolved in a mixture of 150 ml of methanol and 9 ml of 1N HCl and hydrogenated over 0.9 g of a 10% Pd-carbon catalyst at room temperature for 6 hours. Then the catalyst was filtered off, and the filtrate was distilled in vacuo to dryness. The resulting dipeptide was condensed with a mixed anhydride which had been prepared from 1.89 g of Boc-Gly-OH in the same manner as in (1) of Example 2. The product was recrystallized from ethyl acetate-ether, giving 3.09 g of Boc-Gly-Asp-Tyr-OMe; yield 71.8%, m.p. 97°-99° C.

$[\alpha]_D^{24} = -14.1°$ (C=1, methanol)

Anal. Calcd. (%) for C$_{21}$H$_{29}$N$_3$O$_9$: C, 53.96; H, 6.25; N, 8.99. Found (%): C, 53.95; H, 6.68; N, 8.69.

1.83 g of the above obtained tripeptide methyl ester was dissolved in 15 ml of methanol, then 1.08 ml of 90% hydrazine hydrate was added to the solution, and the mixture was stirred at room temperature for 17 hours. Ether was added to the reaction mixture in which a precipitate had formed. The precipitate was filtered, dried, and washed again with 5% acetic acid, giving 1.68 g of Boc-Gly-Asp-Tyr-NHNH$_2$; yield 92.1%, m.p. 149°-151°.

$[\alpha]_D^{25} = -23.6°$ [C=0.5, DMF-acetic acid (1:1)]

Anal. Calcd. (%) for C$_{20}$H$_{29}$N$_5$O$_8$: C, 51.39; H, 6.25; N, 14.98. Found (%): C, 51.14; H, 6.37; N, 15.09.

(2) Synthesis of Boc-Gly-Asp-Tyr-Met-Gly-Trp-Met-Asp-Phe-NH$_2$ 0.885 g (0.001 mole) of Boc-Met-Gly-Trp-Met-Asp-Phe-NH$_2$ [cf. (3) of Example 7] was similarly treated with 6 ml of trifluoroacetic acid containing 0.2 ml of ethandithiol and condensed with 0.701 g of the tripeptide obtained in the preceding (1), in the same manner as in (2) of Example 1 according to the azide process. The product was precipitated by adding 1N citric acid, washed with water, and recrystallized from methanol, giving 0.97 g of Boc-Gly-Asp-Tyr-Met-Gly-Trp-Met-Asp-Phe-NH$_2$; yield 79.5%, m.p. 197°-200° C.

$[\alpha]_D^{24} = -39.5°$ (C=1, DMF)

Anal. Calcd. (%) for C$_{56}$H$_{73}$N$_{11}$O$_{16}$S$_2$·H$_2$O: C, 54.31; H, 6.10; N, 12.44. Found (%): C, 54.13; H, 6.06; N, 12.18.

(3) Synthesis of Gly-Asp-Tyr(SO$_3$H)-Met-Gly-Trp-Met-Asp-Phe-NH$_2$ 0.488 g (0.0004 mole) of the nonapeptide obtained in the preceding (2) was dissolved in a mixture of 10 ml of DMF and 1 ml of pyridine, 0.637 g of a pyridine-sulfuric anhydride complex was added under cooling with ice, and the mixture was stirred at 0° C. for 30 minutes and then at room temperature for 17 hours. The resulting reaction mixture was concentrated in vacuo, and 20 ml of methanol, 20 ml of butanol, and 12 ml of 0.5 M aqueous calcium acetate solution were added to the residue. The resulting precipitate of calcium sulfate was removed by centrifugation, and the supernatant was distilled in vacuo to dryness. The residue was washed with water, and 0.503 g of Boc-Gly-Asp-Tyr(SO$_3$-)-Met-Gly-Trp-Met-Asp-Phe-NH$_2$·Ca salt was obtained.

This sulfated peptide·Ca salt was treated at 0° C. for 30 minutes with 5 ml of trifluoroacetic acid containing 0.1 ml of ethandithiol. The precipitate formed by adding then anhydrous ether to the reaction mixture was filtered and purified by chromatography on a DEAE-Cellulose column (3×7 cm), wherein 1 l of an 0.3 M ammonium carbonate buffer solution (pH 8.5) was used for elution. Thus, 0.243 g of Gly-Asp-Tyr(SO$_3$H)-Met-Gly-Trp-Met-Asp-Phe-NH$_2$ (Compound VIII) was obtained as a lyophilized product; yield 50.8%.

$[\alpha]_D^{25} = -26.2°$ (C=0.5, 1N ammonia)

Anal. Calcd. (%) for C$_{51}$N$_{65}$N$_{11}$O$_{17}$S$_3$·NH$_3$·5H$_2$O: C, 46.85, H, 6.01; N, 12.86. Found (%): C, 46.80; H, 5.86; N, 12.81.

Amino acid analysis by acidolysis:

Asp 2.05 (2), Gly 1.99 (2), Met 2.00 (2), Tyr 0.97 (1), Phe 0.99 (1).

Infrared absorption spectrum: 1050 cm$^{-1}$ (sulfate ester).

EXAMPLE 9

Preparation of β-Ala-Asp-Tyr(SO$_3$H)-Met-Gly-Trp-Met-Asp-Phe-NH$_2$ (Compound IX)

(1) Synthesis of Boc-β-Ala-Asp-Tyr-NHNH$_2$

In the same manner as in (1) of Example 8, 3.25 g of Boc-β-Ala-Asp-Tyr-OMe was obtained from 4.81 g (0.009 mole) of Z-Asp(OBz)-Tyr-OMe and 2.04 g (0.011 mole) of Boc-β-Ala-OH; yield 75.0%, m.p. 88°-90° C.

$[\alpha]_D^{24} = -22.4°$ (C=1, methanol)

Anal. Calcd. (%) for $C_{22}H_{31}N_3O_9$: C, 54.88; H, 6.48; N, 8.73. Found (%): C, 54.97; H, 6.64; N, 8.42.

Also in the same manner as in (1) of Example 8, 1.56 g of the above tripeptide methyl ester was converted into a hydrazide derivative, giving 1.18 g of Boc-β-Ala-Asp-Tyr-NHNH$_2$; yield 75.7%, m.p. 183°–186° C.

$[\alpha]_D^{25} = -38.4°$ [C=0.5, DMF-acetic acid (1:1)]

Anal. Calcd. (%) for $C_{21}H_{31}N_5O_8$: C, 52.38; H, 6.49; N, 14.55. Found (%): C, 52.12; H, 6.47; N, 14.45.

(2) Synthesis of Boc-β-Ala-Asp-Tyr-Met-Gly-Trp-Met-Asp-Phe-NH$_2$

In the same manner as in (2) of Example 8, 0.977 g of Boc-β-Ala-Asp-Tyr-Met-Gly-Trp-Met-Asp-Phe-NH$_2$ was obtained according to the azide method by condensation of 0.885 g of Boc-Met-Gly-Trp-Met-Asp-Phe-NH$_2$ with 0.722 g of the Boc-β-Ala-Asp-Tyr-NHNH$_2$ obtained in the preceding (1); yield 79.1%, m.p. 207°–209° C.

$[\alpha]_D^{24} = -41.0°$ (C=1, DMF)

Anal. Calcd. (%) for $C_{57}H_{75}N_{11}O_{16}S_2$: C, 55.46; H, 6.12; N, 12.48. Found (%): C, 55.65; H, 6.19; N, 12.32.

(3) Synthesis of β-Ala-Asp-Tyr(SO$_3$H)-Met-Gly-Trp-Met-Asp-Phe-NH$_2$

In the same manner as in (3) of Example 8, sulfation, calcium salt formation, deprotection and purification were conducted on 0.494 g (0.4 m mole) of the nonapeptide obtained in the preceding (2), giving 0.243 g of β-Ala-Asp-Tyr(SO$_3$H)-Met-Gly-Trp-Met-Asp-Phe-NH$_2$ (Compound IX); yield 50.1%.

$[\alpha]_D^{24} = -33.2°$ (C=0.5, 1N ammonia)

Anal. Calcd. (%) for $C_{52}H_{67}N_{11}O_{17}S_3 \cdot NH_3 \cdot 4H_2O$: C, 47.92; H, 6.03; N, 12.89. Found (%): C, 48.05; H, 5.64; N, 12.66.

Amino acid analysis by acidolysis:

Asp 2.09 (2), Gly 0.98 (1), Met 2.07 (2), Tyr 1.05 (1), Phe 0.84 (1), β-Ala 0.97 (1).

Infrared absorption spectrum: 1050 cm$^{-1}$ (sulfate ester)

Pharmacological test I (1) Gallbladder contracting activity

This test was in accordance with the method of G. Bertaccini et al. [Br. J. Pharmacol., 34, 291–310 (1968)].

Male Hartley guinea pigs (weighing 400–600 g) was anesthetized with urethane and fixed at the supine position. After laparotomy, the top of the gallbladder was clamped with a Serre-fine which was connected to a FD pickup (model: SB-IT, NIHON KOHDEN KOGYO Co., Ltd.), and the contraction was recorded on a recorder (model: PJB-3012, made by the above company) through a preamplifier (model: RUP-25, made by the above company). A standard solution and the invented peptide solutions were injected into the jugular vein, and the relative potency was determined from the peak height of the gallbladder contraction. Results of the test are shown in Table 1.

TABLE 1

| Peptide | Gallbladder contracting activity Relative potency |
|---|---|
| Compound I | 0 |
| Compound II | 0 |
| Compound III | 8.7 |
| Compound IV | 5.0 |
| Compound V | <1.0 |
| Compound VI | <1.0 |
| Compound VII | <1.0 |
| Compound VIII | 97 |
| Compound IX | 113 |
| CCK - 8 | 100 |

As is shown in Table 1, Compounds VIII and IX exhibited comparable activities with CCK-8 and activities of Compounds III and IV were mild; while Compounds V, VI, and VII exhibited little activity and Compounds I and II no activity.

(2) Accelerating on pancreatic external secretion

Figure 2:
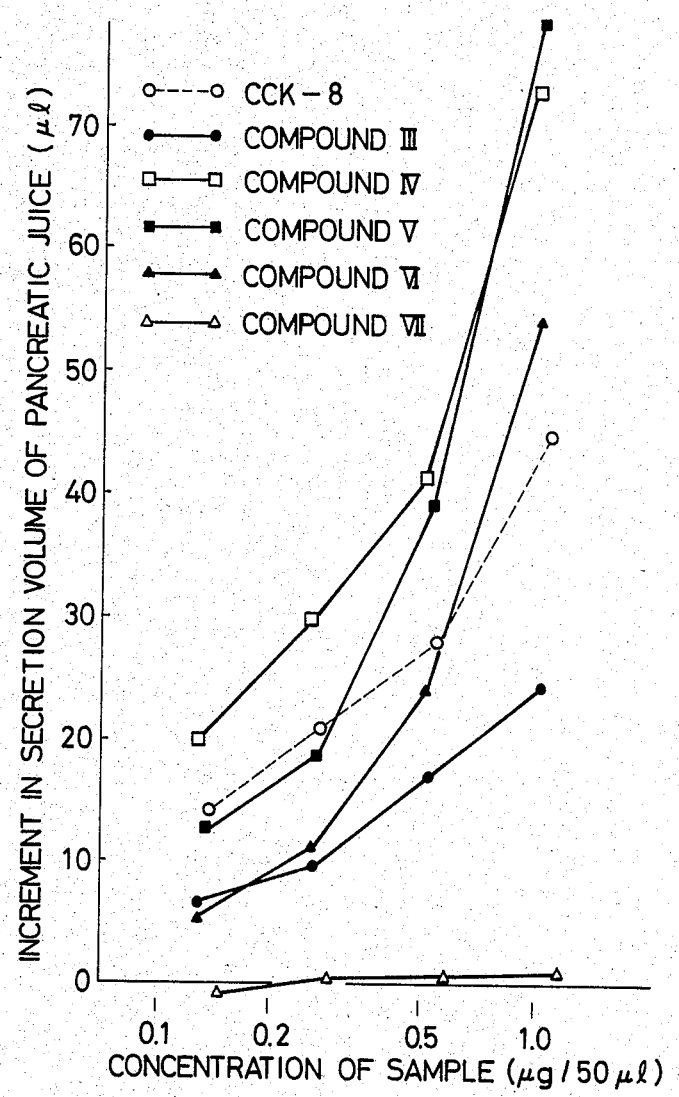
Figure 3:
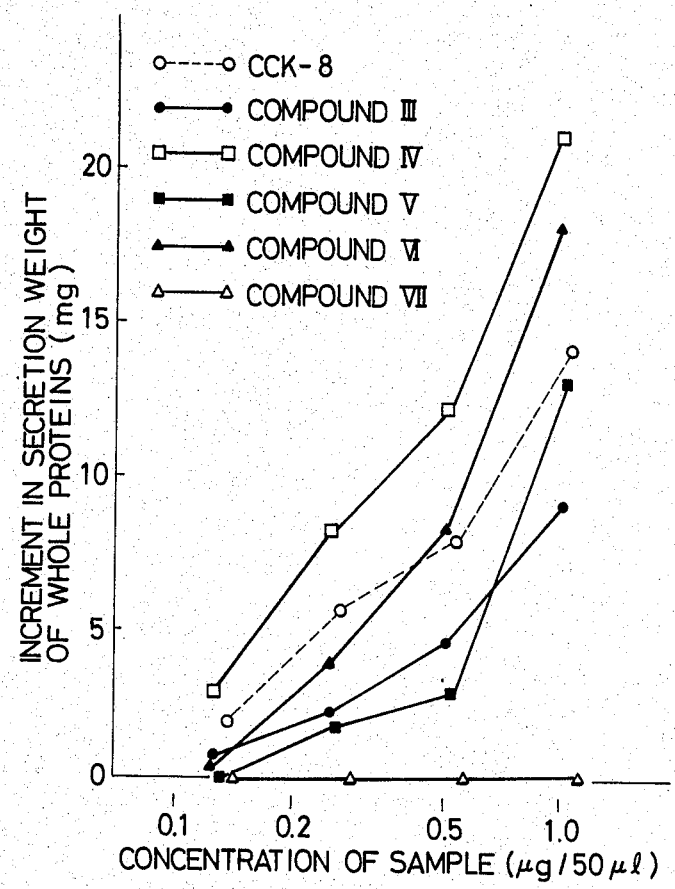
FIGS. 3 and 4 show whole protein secretion accelerating activities of those peptides compared with that of CCK-8.
Figure 4:
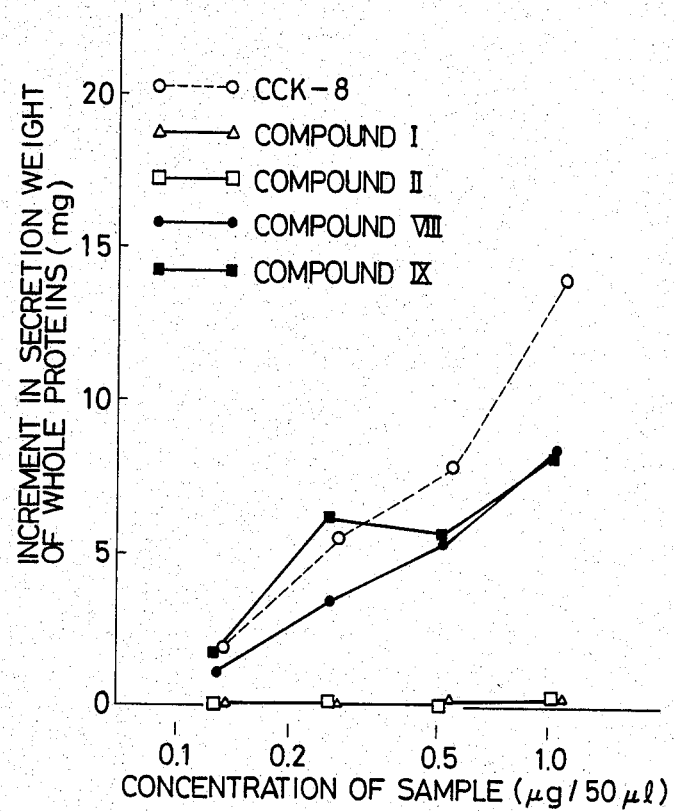

This test was conducted in accordance with the method of Dockray [J. Physiol., 225, 679–692 (1972)]. Male Wistar rats (weighing about 280 g) were deprived for 24 hours and under anesthesia the gastric pylorus and the duodenal side end of the common hepatic duct were ligated. A canula for collection of pancreatic juice was inserted into the duct in the retrograde fashion. The bile was led into the duodenum. Varying concentrations of the control solution (CCK-8 solution) and solutions of the invented peptides in a volume of 50 μl were administered intravenously every one hour, thus determining the increment in the secretion rate of the pancreatic juice and protein during 30 minutes after administration, wherein the amount of the whole protein secreted was determined from the ultraviolet absorbance at 280 nm of the pancreatic juice secreted. Results thereof are shown in FIGS. 1–4.

Referring to the results of the increased amount of the pancreatic juice secreted, the activities of Compounds IV, V, VI, and VIII were comparable to that of CCK-8 and the activity of Compound IX was about half of that of CCK-8, while Compounds I, II, and VII exhibited no active effect.

(3) The use of the Compounds of IV, V, VI, and VII, and the salts of the compounds for accelerating the pancreatic function will be described below.

Firstly, these compounds and salts are mixed with well-known pharmaceutical carriers to prepare pharmaceutical compositions. The carriers include diluents and excipients, e.g., filler, extender, binder, wetting agent, disintegrator, and surfactant, etc. The carriers are selected depending upon a dosage form.

The Compounds of IV, V, VI, and VII, and the salts of the compounds can be contained in the pharmaceutical composition in various amount without restriction. Generally, it is preferable that these compounds and salts are contained in an amount of 1–70 wt. % based on the total composition.

The thus prepared accelerator for pancreatic function is administrated by a method depending upon a dosage form. The administration method is not restricted particularly. For example, tables, pills, solutions, suspensions, emulsions, granules, and capsules are suitable for oral administration; parenteral solutions which contain singly the active ingredient or a mixture of conventional cosolvents such as dextrose and amino acids with the active ingredient are suitable for intravenous injection; the active ingredient is, if necessary, singly administrated intramuscularly, intracutaneously, subcutaneously, or intraperitoneally; suppositories are suitable for rectal administration; and nasal drops are suitable for nasal administration. A suitable dosage range is selected depending upon a using object, the conditions of a patient, and the like. A pharmaceutical composition containing the Compound of IV, V, VI, or VII, or a salt of the compounds is administrated to a human being of weight 60 kg for 1-4 times per day in an amount of about 4 μg to 2 mg of the compound or the salt thereof per kg of body weight per day. With regard to acute toxicity, even when the compound or a salt of the compounds was subcutaneously injected to a mouse in a dose of 2 mg/kg, no toxicity was observed.

EXAMPLE 10

Preparation of
Glt-Ala-Tyr(SO$_3$H)-Gly-Trp-Met-Asp-Phe-NH$_2$
(Compound X)

(1) Synthesis of Glt-Ala-Tyr-Gly-Trp-Met-Asp-Phe-NH$_2$ 1.00 g of Boc-Ala-Tyr-Gly-Trp-Met-Asp-Phe-NH$_2$ (m.p. 197°-200° C. Anal. Calcd. (%) for C$_{48}$H$_{61}$N$_9$O$_{12}$S: C, 58.35; H, 6.22; N, 12.75. Found (%): C, 58.35; H, 6.43; N, 12.61) was dissolved in 5 ml of trifluoroacetic acid containing 0.2 ml of ethanedithiol and reacted at room temperature for 30 minutes. Then 100 ml of anhydrous ether was added to the reaction mixture, and the resulting precipitate was filtered and dried. This deprotected heptapeptide was dissolved in 20 ml of DMF containing 0.14 ml of triethylamine, and 0.40 g of glutaric anhydride was added under cooling with ice. After 17-hour stirring at 4° C., the reaction mixture was distilled in vacuo to remove the solvent, and 1N citric acid was added to the residue to form a precipitate. It was washed with water and recrystallized from 20 ml of methanol, giving 0.77 g of Glt-Ala-Tyr-Gly-Trp-Met-Asp-Phe-NH$_2$; yield 76.1%, m.p. 167°-170° C.

$[\alpha]_D^{24} = -38.5°$ (C=1, DMF)

Anal. Calcd. (%) for C$_{48}$H$_{59}$N$_9$O$_{13}$S: C, 57.53; H, 5.93; N, 12.58. Found (%): C, 57.42; H, 5.99; N, 12.22.

(2) Synthesis of Glt-Ala-Tyr(SO$_3$H)-Gly-Trp-Met-Asp-Phe-NH$_2$ 301 mg of the acylated peptide obtained in the preceding (1) was dissolved in a mixture of 10 ml of DMF and 1 ml of pyridine, and 477 mg of a pyridine-sulfuric anhydride complex was added under cooling with ice. The mixture was stirred at 0° C. for 30 minutes and then at room temperature for 20 hours. The reaction mixture was concentrated in vacuo, 30 ml of 0.05 M aqueous ammonium carbonate solution was added to the residue, and the pH was adjusted to 8.5 with aqueous ammonia. The solution was purified by chromatography on a DEAE-Cellulose column (4 cm×12 cm), wherein the adsorption and washing was carried out by using 500 ml of an 0.05 M buffer solution of ammonium carbonate-ammonium bicarbonate (pH 8.5) and the elution by using 700 ml of the same but 0.2 M buffer solution (pH 8.5). The active fractions eluted were collected, concentrated, and lyophilized, giving 163 mg of Glt-Ala-Tyr(SO$_3$H)-Gly-Trp-Met-Asp-Phe-NH$_2$ (Compound X); yield 50.2%.

Anal. Calcd. (%) for C$_{48}$H$_{59}$N$_9$O$_{16}$S$_2$·NH$_3$·4H$_2$O: C, 49.22; H, 6.02; N, 11.96. Found (%): C, 49.22; H, 5.79; N, 12.12.

Amino acid analysis by acidolysis:

Asp 1.05 (1), Gly 0.96 (1), Ala 1.02 (1), Met 0.94 (1), Tyr 1.00 (1), Phe 0.98 (1).

Infrared absorption spectrum: 1050 cm$^{-1}$ (sulfate ester).

EXAMPLE 11

Preparation of
pGlu-Ala-Tyr(SO$_3$H)-Gly-Trp-Met-Asp-Phe-NH$_2$
(Compound XI)

(1) Synthesis of pGlu-Ala-Tyr-Gly-Trp-Met-Asp-Phe-NH$_2$ 1.51 g of Boc-Gly-Trp-Met-Asp-Phe-NH$_2$ was dissolved in 5 ml of trifluoroacetic acid containing 0.2 ml of ethandithiol, and reacted at room temperature for 30 minutes. Then 100 ml of anhydrous ether was added to the reaction mixture, and the resulting precipitate was filtered and dried. This pentapeptide, dissolved in 20 ml of DMF containing 0.28 ml of triethylamine, was condensed with 0.76 g of pGlu-Ala-Tyr-NHNH$_2$ [m.p. 269°-270° C. Anal. Calcd. (%) for C$_{17}$H$_{23}$N$_5$O$_5$: C, 54.10; H, 6.14; N, 18.56. Found (%): C, 54.00, H, 6.28; N, 18.74] according to the azide method wherein, the hydrazide was reacted after being converted with isoamyl nitrite into the azide. Then the solvent was distilled off in vacuo, and 1N citric acid was added to the residual liquid to form a precipitate. It was washed with water and recrystallized from dimethylformamide-methanol, giving 1.68 g of pGlu-Ala-Tyr-Gly-Trp-Met-Asp-Phe-NH$_2$; yield 84.1%, m.p. 207°-209° C.

$[\alpha]_D^{24} = -34.9°$ (C=1, DMF)

Anal. Calcd. (%) for C$_{48}$H$_{58}$N$_{10}$O$_{12}$S: C, 57.70; H, 5.85; N, 14.02. Found (%): C, 57.60; H, 6.15; N, 14.15.

(2) Synthesis of pGlu-Ala-Tyr(SO$_3$H)-Gly-Trp-Met-Asp-Phe-NH$_2$ 1.00 g of the octapeptide obtained in the preceding (1) was dissolved in a mixture of 10 ml of DMF and 1 ml of pyridine, 1.60 g of a pyridine-sulfuric anhydride complex was added under cooling with ice, and the mixture was stirred at 0° C. for 30 minutes and then at room temperature for 17 hours. The resulting reaction mixture was concentrated in vacuo, 50 ml of an 0.05 M aqueous ammonium carbonate solution was added to the residue, and the pH was adjusted to 8.5 by adding aqueous ammonia. The solution was purified by ion exchange chromatography on a DEAE-Cellulose column (4 cm×12 cm). The active fractions eluted were collected, concentrated, and lyophilized, giving 563 mg of pGlu-Ala-Tyr(SO$_3$H)-Gly-Trp-Met-Asp-Phe-NH$_2$ (Compound XI), yield 52.2%.

Anal. Calcd. (%) for C$_{48}$H$_{58}$N$_{10}$O$_{15}$S$_2$·NH$_3$·4H$_2$O: C, 49.35; H, 5.95; N, 13.19. Found (%): C, 49.51; H, 5.95; N, 13.02.

Amino acid analysis by acidolysis:

Asp 1.05 (1), Glu 0.96 (1), Gly 1.04 (1), Ala 0.98 (1), Met 1.00 (1), Tyr 1.03 (1), Phe 0.94 (1).

Infrared absorption spectrum: 1050 cm$^{-1}$ (sulfate ester).

Pharmacological test II (1) Gastric acid secretion accelerating activity

This test was conducted with Shay rats [H, Shay et al., Gastroenterology, 5, 43 (1945)] prepared. Employing male Wistar rats (weighing 270-310 g) deprived for 24 hours, the gastric pylorus was ligated under ether-anesthesia. Immediately thereafter, the invented peptides and tetragastrin as a control were administered intravenously. Gastric juice was withdrawn 2 hours after administration, and its amount and the total amount of acid secreted were measured to determine the relative potency based on tetragastrin. Results of the test are shown in Table 2.

TABLE 2

| Gastric acid secretion accelerating activity | |
|---|---|
| Peptide | Relative potency |
| Compound X | 6.1 |
| Compound XI | 2.0 |
| Tetragastrin | 1.0 |

(2) Pancreatic external secretion accelerating activity

The test was conducted in the same manner as stated already. The increment in the secretion rate of the protein in the pancreatic during 30 minutes after administration of the test solution was determined from the ultraviolet absorbance at 280 nm of the pancreatic juice. The found values were compared with that of tetragastrin. Results thereof are shown in Table 3.

TABLE 3

| Pancreatic external secretion accelerating activity | |
|---|---|
| Peptide | Relative potency |
| Compound X | 258.8 |
| Compound XI | 50.0 |
| Tetragastrin | 1.0 |

What is claimed is:

1. Novel peptides represented by the following formula $$R_1\text{-A-B-C-D-Trp-Met-Y} \quad (1)$$

wherein $R_1$ denotes pGlu, X—$R_2$—CO—, X being carboxyl or amino and $R_2$ being lower alkylene of 1–6 carbon atoms, or

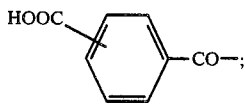

A denotes Asp, Ala, or merely a chemical bond; B denotes Tyr(SO$_3$H) or Phe(NHSO$_3$H); C denotes Met or merely a chemical bond; D denotes Gly, D-Ala, or D-Trp; and Y denotes NH$_2$, Asp-NH$_2$, or Asp-Phe-NH$_2$; with the proviso that Y is NH$_2$ or Asp-NH$_2$ when $R_1$ is pGlu, HOOC—$R_2$—CO—, or

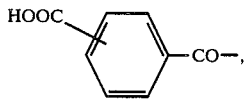

B is Tyr(SO$_3$H), C is Met, and D is Gly, and pharmacologically acceptable salts thereof.

2. Novel peptides and pharmacologically acceptable salts thereof according to claim 1, wherein $R_1$ is NH$_2$—$R_2$—CO—, $R_2$ being lower alkylene of 1–6 carbon atoms.

3. The novel peptides and pharmacologically acceptable salts thereof according to claim 1, wherein B is Phe(NHSO$_3$H).

4. Novel peptides and pharmacologically acceptable salts thereof according to claim 1, wherein D is D-Ala or D-Trp.

5. The novel peptides and pharmacologically acceptable salts thereof according to claim 1, wherein Y is NH$_2$ or Asp-NH$_2$.

6. The novel peptides and pharmacologically acceptable salts thereof according to claim 1, wherein $R_1$ is p-Glu, X—$R_2$—CO—, X being carboxyl group or amino group and $R_2$ being lower alkylene group of 1–6 carbon atoms, or

A is Ala, and C is merely a chemical bond.

7. The pharmacologically acceptable salts according to claim 1, which is selected from the group consisting of alkali metal salts, alkali earth metal salts, organic amine salts, and ammonium salt.

8. Novel peptide according to claim 2 of the formula

Gly-Asp-Tyr(SO$_3$H)-Met-Gly-Trp-Met-Asp-Phe-NH$_2$ and pharmacologically acceptable salts thereof.

9. Novel peptide according to claim 2 of the formula

Beta-Ala-Asp-Tyr(SO$_3$H)-Met-Gly-Trp-Met-Asp-Phe-NH$_2$ and pharmacologically acceptable salts thereof.

10. Novel peptide according to claim 3 of the formula

Suc-Phe(NHSO$_3$H)-Met-Gly-Trp-Met-Asp-Phe-NH$_2$ and pharmacologically acceptable salts thereof.

11. Novel peptide according to claim 4 of the formula

Suc-Tyr(SO$_3$H)-Met-D-Ala-Trp-Met-Asp-Phe-NH$_2$ and pharmacologically acceptable salts thereof.

12. Novel peptide according to claim 4 of the formula

Suc-Tyr(SO$_3$H)-Met-D-Trp-Trp-Met-Asp-Phe-NH$_2$ and pharmacologically acceptable salts thereof.

13. Novel peptide according to claim 4 of the formula

Glt-Tyr(SO$_3$H)-Met-D-Trp-Trp-Met-Asp-Phe-NH$_2$ and pharmacologically acceptable salts thereof.

14. Novel peptide according to claim 4 of the formula

Pht-Tyr(SO$_3$H)-Met-D-Trp-Trp-Met-Asp-Phe-NH$_2$ and pharmacologically acceptable salts thereof.

15. Novel peptide according to claim 5 of the formula

Suc-Tyr(SO$_3$H)-Met-Gly-Trp-Met-NH$_2$ and pharmacologically acceptable salts thereof.

16. Novel peptide according to claim 5 of the formula

Suc-Tyr(SO$_3$H)-Met-Gly-Trp-Met-Asp-NH$_2$ and pharmacologically acceptable salts thereof.

17. Novel peptide according to claim 6 of the formula

Glt-Ala-Tyr-(SO$_3$H)-Gly-Trp-Met-Asp-Phe-NH$_2$ and pharmacologically acceptable salts thereof.

18. Novel peptide according to claim 6 of the formula pGlu-Ala-Tyr(SO$_3$H)-Gly-Trp-Met-Asp-Phe-NH$_2$ and pharmacologically acceptable salts thereof.

19. Pharmaceutical composition for accelerating pancreatic function comprising an effective accelerating amount of a compound of claim 1 and a pharmaceutically acceptable carrier.

* * * * *